(12) United States Patent
Adjani et al.

(10) Patent No.: US 7,762,997 B2
(45) Date of Patent: Jul. 27, 2010

(54) HYGIENIC AND THERAPEUTIC VAGINAL CLEANSING AND HYDROMASSAGING DEVICE

(76) Inventors: Ariana Adjani, 1 Carters Lane, London (GB) SE23 2TS; Simon Allen, 1 Carters Lane, London (GB) SE23 2TS ( * ) Notice: Subject to any disclaimer, the term of this patent is extended or adjusted under 35 U.S.C. 154(b) by 594 days.

(21) Appl. No.: 10/967,353

(22) Filed: Oct. 19, 2004

(65) Prior Publication Data
US 2006/0084895 A1 Apr. 20, 2006

(51) Int. Cl.
- A61M 3/02 (2006.01)
- A61M 31/00 (2006.01)
- A61H 9/00 (2006.01)
- A61H 7/00 (2006.01)
- A61H 19/00 (2006.01)

(52) U.S. Cl. .................. 604/279; 604/39; 601/160; 601/165

(58) Field of Classification Search ............... 604/39, 604/212, 257, 279, 523, 537, 515, 911; 601/154–155, 601/160–161, 165, 169
See application file for complete search history.

(56) References Cited

U.S. PATENT DOCUMENTS

| | | | | |
|---|---|---|---|---|
| 2,106,433 A | * | 1/1938 | Morse | 604/109 |
| 2,139,653 A | * | 12/1938 | Belfrage | 604/39 |
| 2,147,652 A | * | 2/1939 | Kennison | 604/39 |
| 2,243,299 A | * | 5/1941 | Travers | 604/39 |
| 2,591,371 A | * | 4/1952 | Nimmo | 604/39 |
| 3,581,743 A | * | 6/1971 | Stein et al. | 604/111 |
| 4,068,663 A | * | 1/1978 | D'Alessandro | 604/200 |
| 4,336,801 A | * | 6/1982 | Sentell et al. | 604/31 |
| 5,102,387 A | * | 4/1992 | Jorde | 604/39 |
| 2003/0212382 A1 | * | 11/2003 | Abbott et al. | 604/517 |

\* cited by examiner

*Primary Examiner*—Justine R Yu
*Assistant Examiner*—Kristen C Matter

(57) ABSTRACT

A unique construction of this douche ensures that the incoming and outgoing streams of cleansing liquid do not mix inside the device. Thus it provides a superior cleansing of the vagina. The device has two parts: an inner core and an outer casing, which so snap fit together that create two isolated spaces inside the device securing no leakage between them. The parts are easily separable for cleaning purposes. The base of the device is round so, when placed against the entrance of the vagina, it acts as a plug. The base has two pipe connectors for a cleansing liquid, an inlet and an outlet, and these are interchangeable. A stream of liquid passing through the device smoothes out folds of the vagina, covering its entire surface, and thus ensures Improved hygiene and therapy. This douching device simultaneously provides vaginal hydromassage, which can be enhanced by manually compressing the outlet.

3 Claims, 6 Drawing Sheets

HYGIENIC AND THERAPEUTIC VAGINAL CLEANSING AND HYDROMASSAGING DEVICE

DESCRIPTION OF THE INVENTION

The present invention relates to a hygienic and therapeutic vaginal cleansing and hydromassaging device.

Women have used different devices for the vaginal irrigation, ranging from a rubber bulb to the latest models of irrigation appliances, such as the "Irrigating appliance for female hygiene", which received the U.S. Pat. No. 4,287,888 in Sep. 8, 1981 and the "Vaginal irrigation apparatus", U.S. Pat. No. 4,309,995 in Jan. 12, 1982. These appliances allowed for the vaginal irrigation to be done manually with a limited amount of water or other fluids. Each subsequent irrigation device was constructed to improve the earlier model.

Previously, injectors were made of metal, which caused vaginal discomfort during insertion and use. Subsequent injectors were covered with a soft cellular foam material. Separate parts were made from different materials, which were difficult to keep clean, thus subjecting women to the risk of infections, and were often difficult to use. All of them have the same disadvantage—they were unable to smooth out the folds of the vagina for thorough bathing, and a cleansing liquid enters and exits the vagina simultaneously. This means that irrigation cannot cover the whole surface of the vagina and, therefore, can not cleanse or treat it completely. The vaginal hydromassage has previously been overlooked.

According to the present invention there is provided a two-part vaginal cleansing and hydromassaging device comprising a generally circular and flat base region of such configuration as in use to close the entrance to the vagina and create a plug; the first part being an outer casing extending from the base region to a tip region, and having a conical wall portion extending from a periphery of the base region for a substantial part of the length of the outer casing towards the tip region, followed by a cylindrical wall portion ending with the tip region; the second part being an inner core comprising the base region and a generally cylindrical wall extending from a centre of the base region towards the tip region and defining two isolated spaces inwardly from the outer casing; the two isolated spaces comprising a central pipe being inward from the cylindrical wall portion of the outer casing and the cylindrical wall of the inner core, and a reservoir space being between the conical wall portion of the outer casing and outward from the inner core a central pipe connector at the centre of the base region communicating with the central pipe and a side pipe connector at a side of the base region communicating with the reservoir space; where one of the pipe connectors being an inlet for cleansing liquid and the other being an outlet for circulated cleansing liquid; a plurality of openings in the conical wall portion and an opening at the tip, the openings in the conical wall portion being spaced a distance from the base region, which distance is substantially less than the distance between the openings in the conical wall portion and the opening at the tip to enable the cleansing liquid to circulate effectively within the vagina; wherein the openings in the conical wall portion communicate with the side pipe connector, and the tip opening communicates with the central pipe connector; and the device is such that in use incoming and outgoing cleansing liquid do not mix in the device; the first and second parts being a snap fit together and easily separable for cleaning purposes such that the first and second parts so fit together that the isolated spaces are all times separate to ensure no leakage between them.

The side pipe connector and the pipe connector at the centre of the base region may be the same size.

The inner core and the outer casing when assembled may form a seal to create the two isolated spaces within the device.

The vaginal cleansing and hydromassaging device may comprise a high-density polypropylene.

The base of this douching device fits against the entrance of a vagina and acts as a plug. The cleansing liquid enters the vagina from the inlet, fills the cavity of the vagina smoothing out its folds, and then exits via the outlet. Thus the device improves vaginal cleansing, as the stream of cleansing liquid effectively covers the entire surface of the vagina, and ensures the therapy. A simultaneous vaginal hydromassage provided by this device makes it a superior douche. It is possible to increase the pressure of water or liquid entering the vagina by intermittently closing the outlet of the device manually. This is an enhanced way of hydromassaging the vagina and the adjacent organs. In addition, it increases sensitivity and tones the muscles.

Further effectiveness can be achieved by deep breathing, which makes the abdominal wall expand and contract resulting in deep relaxation and stimulation of the nervous and hormonal systems leading to overall rejuvenation. The hygienic and therapeutic vaginal cleansing and hydromassaging device is recommended to all women for the daily hygienic use and for the treatment of the following chronic diseases: vaginitis, erosion of cervix of the uterus, leucorrhoea, infertility, frigidity, vaginism, etc. Additionally it can be used for contraceptive purposes. Following a sexual intercourse, abundant bathing with the vaginal cleansing and hydromassaging device can be beneficial.

Embodiments of the invention can have dimensions that are effective and suitable for almost every woman. The plastic transfer tubes fit the inlet port and optionally can be fitted to the outlet port for drainage. It is also possible to fit the liquid supplier tube to a bathroom shower, mixer tap or reservoir bag with water or cleansing liquid. For hydromassaging purposes, best results are achieved when the device is connected to a shower or douche tube. For medical purposes, it is preferable to use the containers in the format of plastic bags because antiseptic, drug or aromatic substances are best handled this way. The reservoir bag filled with water or cleansing liquid should be placed above the device, with the distance being preferably around 70 cm.

Embodiments of the invention can be used in seated or laying position. The most comfortable way to use the hygienic and therapeutic vaginal cleansing and hydromassaging device is to lay in a bath filled with warm water (with the temperature of up to 40° C.). The user should relax her muscles and gently fit the device into her vagina. For the purpose of hydromassage, the user should intermittently increase the pressure inside the vagina using her finger or plastic plug, closing the outlet that allows the flow of liquid out of the device. It is suggested that the woman should control the device with her hand, particularly during hydromassaging. By changing the feeder tube from the inlet port to the outlet port, a different sensation is experienced.

A pump with a non-return valve could be used for hydromassaging purposes. This would involve applying the pump to the inlet of the device and flushing bath water directly into the vagina, thus avoiding variations in temperature of the water, which may happen when applying water directly from the shower. The duration of the hydromassaging procedure should be 10-20 minutes.

A disposable vaginal cleansing and hydromassaging set can be used for cleansing the vagina under the pressure of water that dilates and smoothes out the folds inside the vagina. It may be constructed out of plastic and comprise the device, a pipe and a plastic bag with volume of up to 1 liter. The bag may contain water, with or without antiseptic or aromatic liquid. The bag has a tap or a clip attached to its outlet, which connects to the upper end of the tube. There may be a small tap in the upper end of the tube, which allows the water or liquid to flow into vagina; and the connection tube may have a non-return valve. For hydromassage, the plastic bag should be compressed. This is why the walls of the plastic bag in the middle part may be thickened. One outlet may be closed intermittently with a plug or finger. The procedure of using the device is simple and can be done in sitting or laying positions. After inserting the device into the vagina, the user opens a small tap and water or liquid runs to into the vagina under the force of gravity. The user may compress the bag to increase the pressure of water inside the vagina, releasing the pressure afterwards. For quick bathing and hydromassaging (for example, after menses), the use of the simple disposable vaginal set is recommended. The set may comprise the following components made of plastic: the device, the transfer tube and the bag. The device has only one inlet port and there is no partition inside. The user should compress the bag increasing the pressure of the water inside the vagina a few times. During the procedure some water will come back to the tube. The user should compress the bag periodically and after remove the injector from the vagina allowing the water to flow out of the body.

The present invention ensures thorough hygienic cleansing and therapy, and at the same time provides an effective hydromassage of the vagina with the circulating stream of water or liquid, without mixing the incoming and outgoing water or liquid in the device. Overall its use results in improved health combined with pleasure.

Embodiment of the present invention will now be described by way of example and with reference to the accompanying drawing in which.

Figure 1:
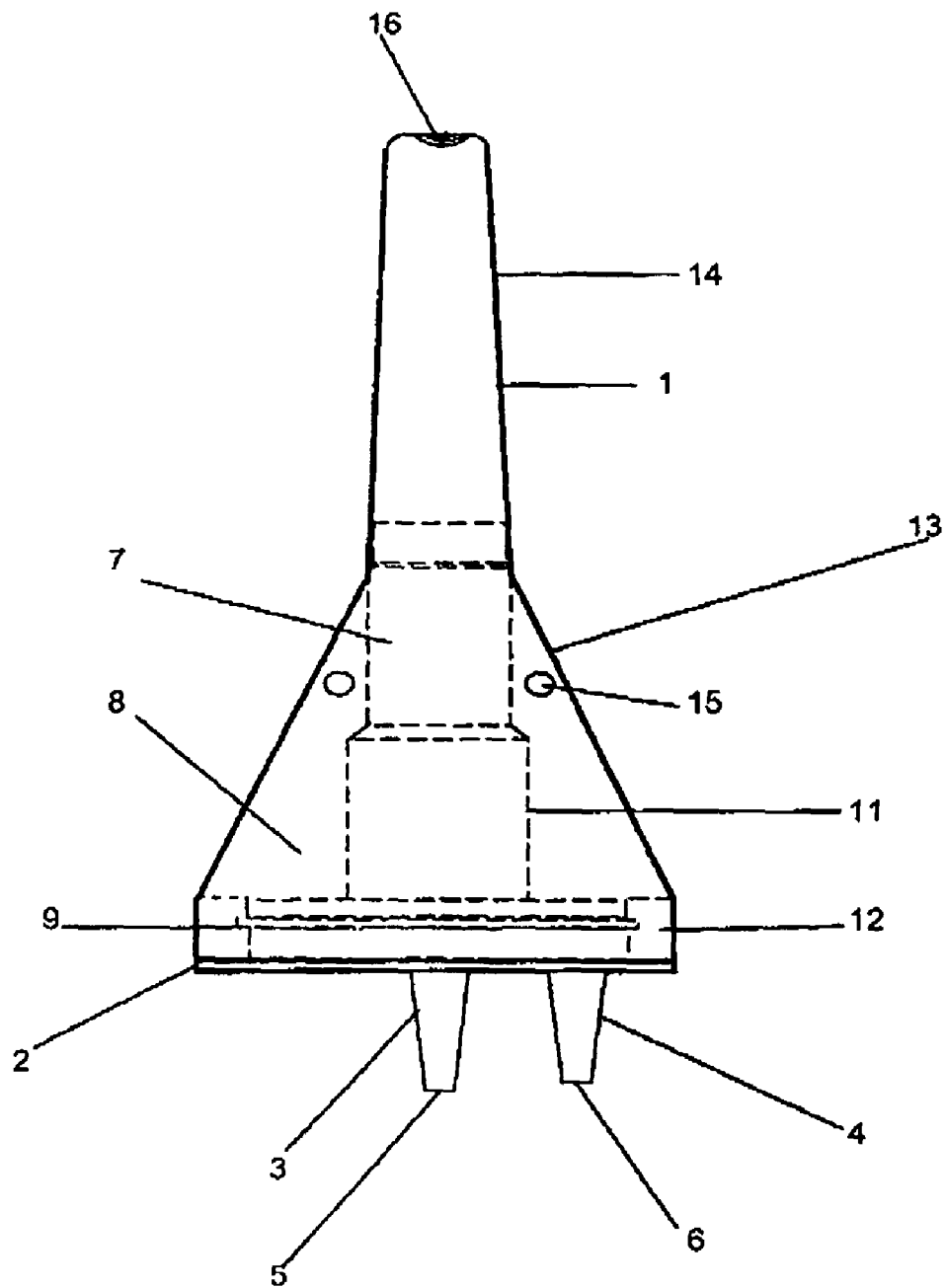
FIG. 1 is a front view of a vaginal cleansing and hydromassaging device, showing the inside details.

As shown in FIG. 1, the device 1 comprises two parts: an outer casing and inner core, which are joined together in such a way that it becomes a single unit. On the base 2 of the device are two pipe connectors 3 and 4 with connections for transfer tubes. Holes 1 and 2 from these pipe connectors lead to a central pipe 7 and to a reservoir space 8. A snap lock 9 joins together the outer casing and the inner core. The central pipe 7 has a base part 11. The external part of the device comprises the base 12 of the outer casing which passes to a conical wall portion 13 of the outer casing and further to a cylindrical portion 14 of the device. Between the central pipe 7 of the inner core and the conical wall portion 13 of the outer casing there is the reservoir space 8. This space drains through holes 15 in the conical wall portion 13. The cylindrical wall portion is open ended at its tip region 16.

Figure 2:
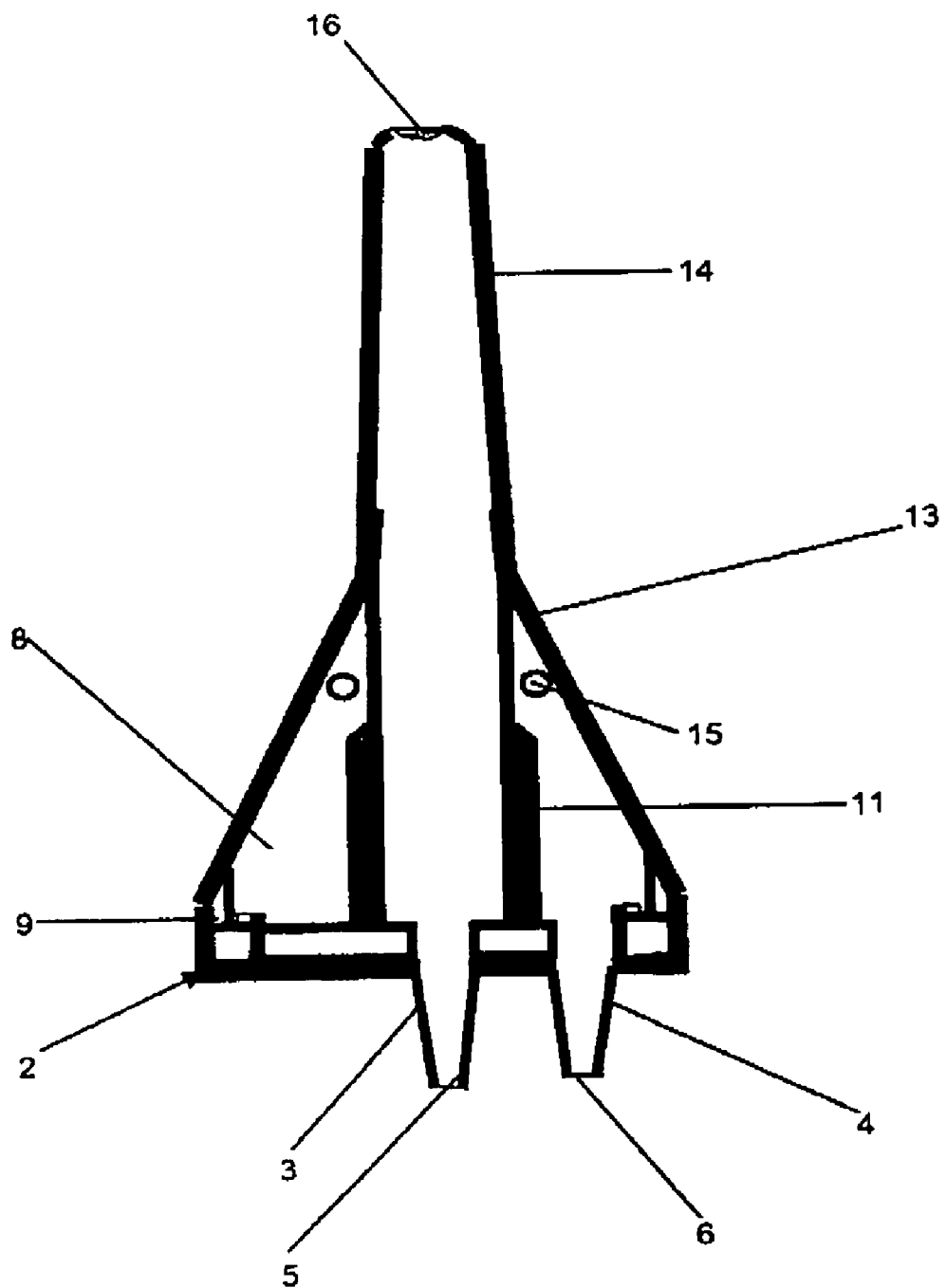
FIG. 2 is a cross section of the vaginal cleansing and hydromassaging device.

As will be seen in FIG. 2, in the cross section of the device, there are two cavities: the central pipe 7 and the reservoir space 8, which are isolated from each other. The inlet pipe connector 3 connects only with the central pipe 7, and the outlet pipe connector 4 connects only with reservoir space 8. The base part 11 of the central pipe 7 is strengthened. This makes the base of the inner core rigid and the snap lock 9 stronger. The holes 15 on the side of the outer casing connect only with the reservoir space 8.

Figure 3:
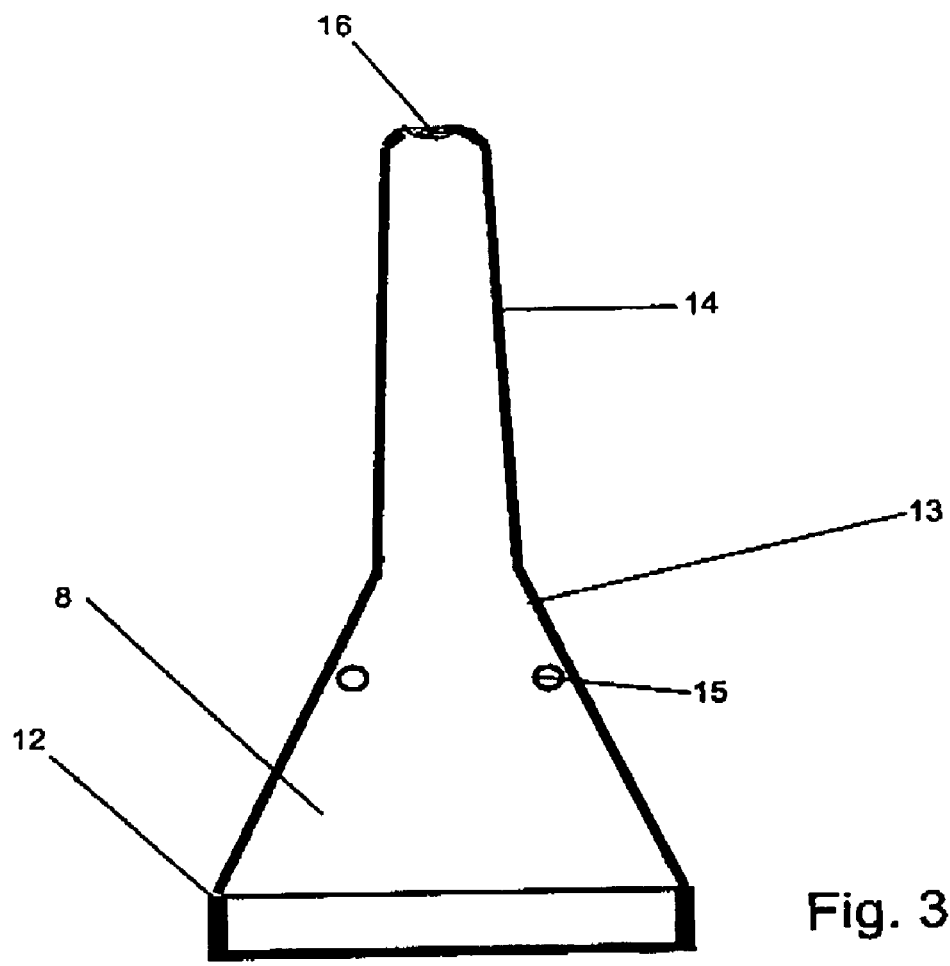
FIG. 3 is a front view of outer casing.
Figure 4:
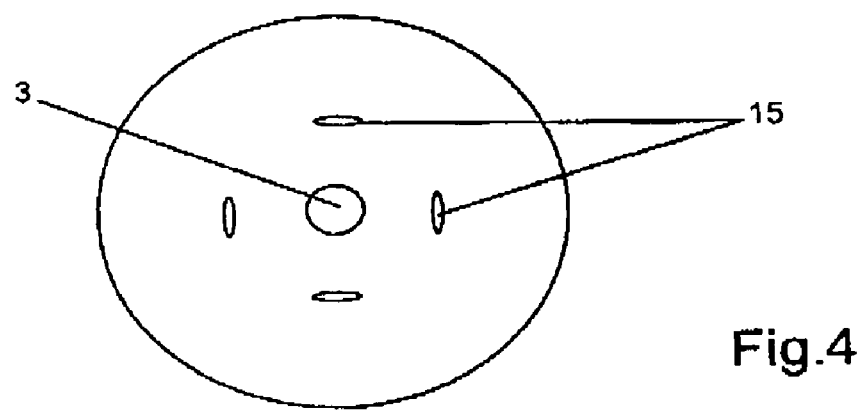
FIG. 4 is a plan view of outer casing.

As shown in FIG. 3 the outer casing narrows from the base 12 to the tip region 16. The length of the outer casing is about 11 cm. On the plan view of the outer casing shown in FIG. 4 there are illustrated four holes 15 around the side and a hole in the centre, at the tip region 16 of the cylindrical wall portion.

Figure 5:
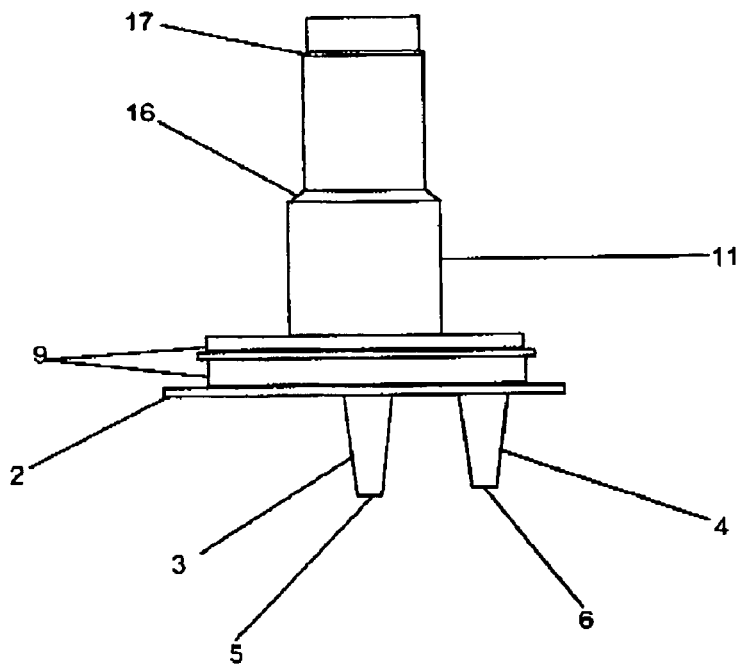
FIG. 5 is a front view of inner component.
Figure 6:
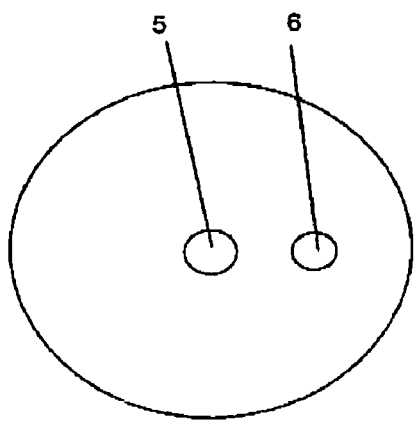
FIG. 6 is an underside view of inner core.
Figure 7:
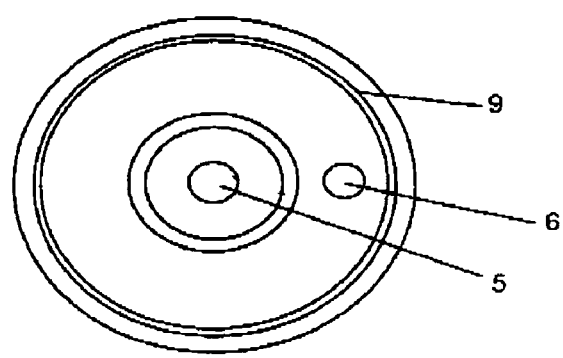
FIG. 7 is a planar view of inner core.

FIG. 5, FIG. 6 and FIG. 7 show different views of the inner core. FIG. 5 shows that the diameter of the central pipe is reduced (reference numerals 16 and 17), which hermetically seals the joint at the end part of the inner core with the tip of the outer casing (see FIG. 1 and FIG. 2). The snap lock 9 is constructed in such a way that it automatically seals the joint; in addition, it is easy to use. The diameter of the base 2 of the inner core is advantageously 5 cm, which is enough to close the entrance of the vagina.

Figure 8:
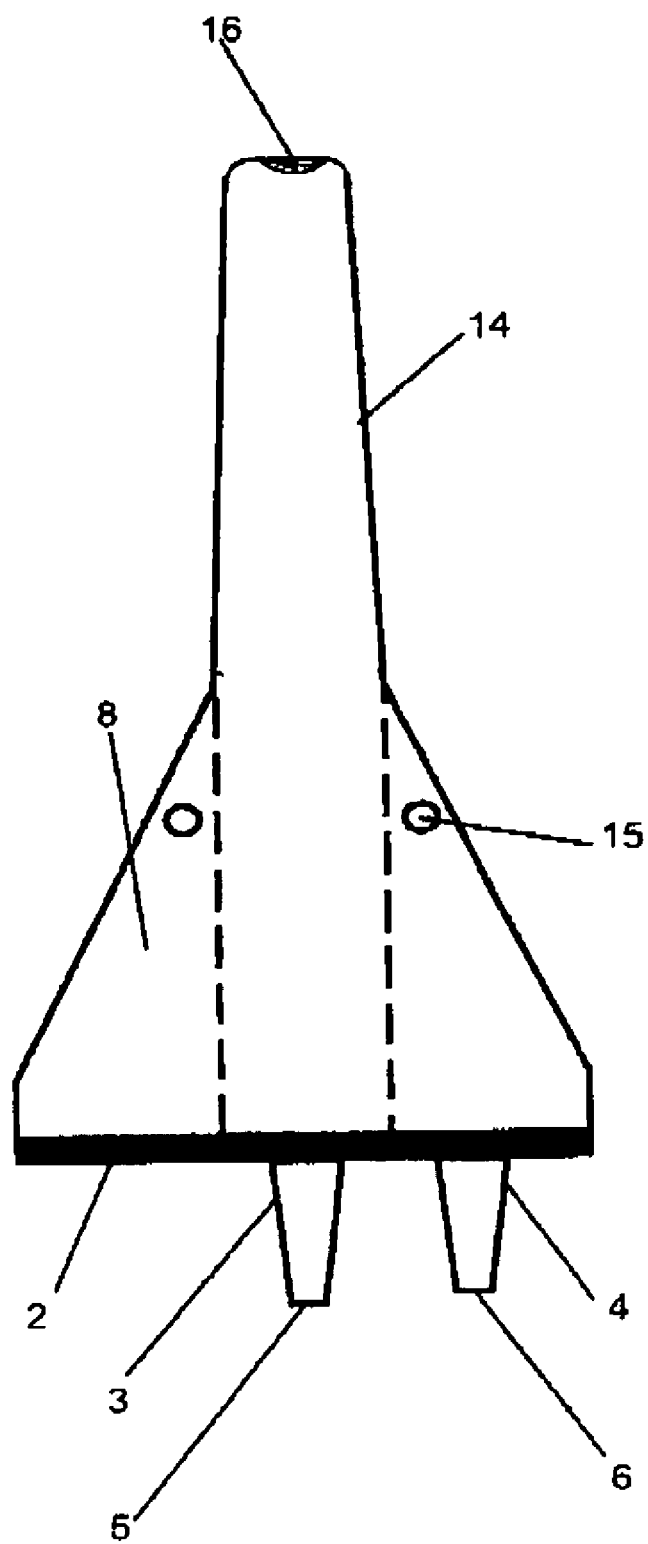
FIG. 8 is a front view of the device from the disposable vaginal cleansing and hydromassaging set.
Figure 9:
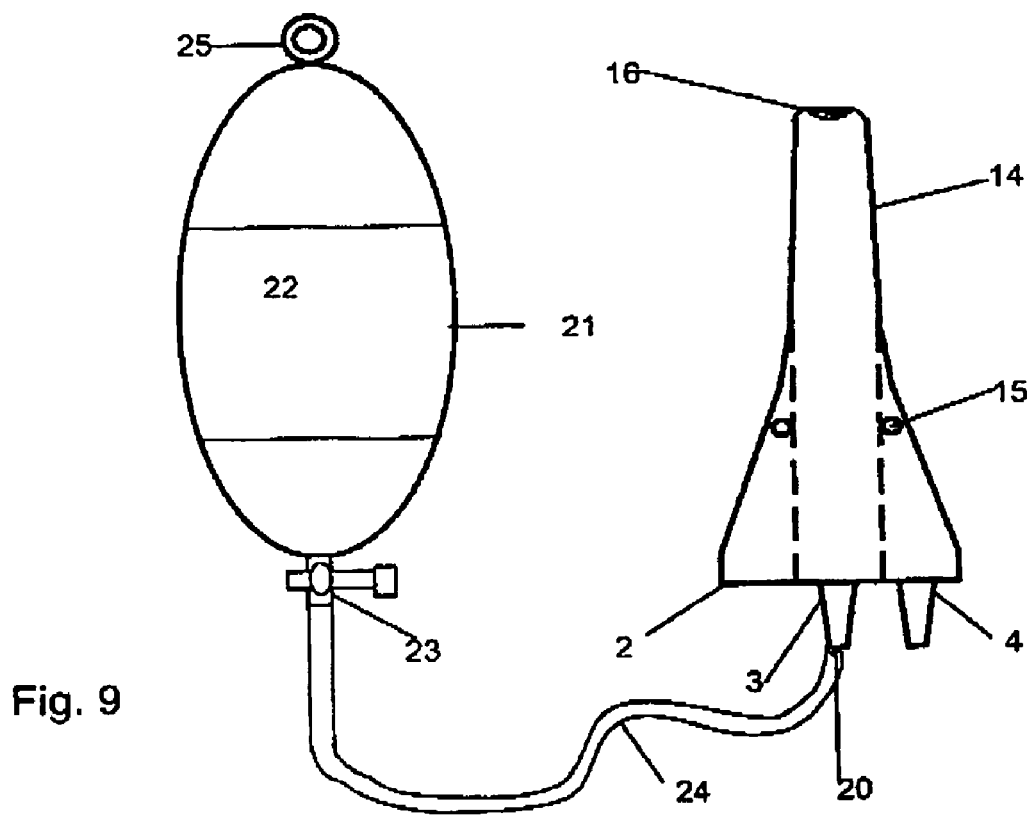
FIG. 9 is a front view of the disposable vaginal cleansing and hydromassaging set: device, the tube and a bag.

FIG. 8 shows a single device from the disposable vaginal cleansing and hydromassaging set together with the internal details. The holes 5 and 6 direct liquid through the inlet and outlet pipe connectors 3 and 4 to the separate cavities of the central pipe and the reservoir space 8. The device should be used as shown in FIG. 9. The device is connected to a plastic bag 21 through the plastic supply tube 24. This bag is a reservoir for water or liquid and can be hung by the noose 25. The walls of the middle part of the bag may be thickened 22, to prevent it from damage when compressed. A lock 23 should be opened to pour the water or liquid from the bag. To prevent the return of water, a non-return valve 20 is placed inside the tube connected it to the device.

The invention claimed is:

1. A two-part vaginal cleansing and hydromassaging device comprising a generally circular and flat base region of such configuration as in use to close the entrance to the vagina and create a plug;

a first part being an outer casing extending from the base region to a tip region, and having a conical wall portion extending from a periphery of the base region for a substantial part of the length of the outer casing towards the tip region, followed by a cylindrical wall portion ending with the tip region;

a second part being an inner core comprising the base region and a generally cylindrical wall extending from a centre of the base region towards the tip region and defining two isolated spaces inwardly from the outer casing;

the two isolated spaces comprising a central pipe being inward from the cylindrical wall portion of the outer casing and the cylindrical wall of the inner core, and a reservoir space being between the conical wall portion of the outer casing and outward from the inner core;

a central pipe connector at the centre of the base region communicating with the central pipe and a side pipe connector at a side of the base region communicating with the reservoir space;

one of the pipe connectors being an inlet for cleansing liquid and the other being an outlet for circulated cleansing liquid;

a plurality of openings in the conical wall portion and an opening at the tip, the openings in the conical wall portion being spaced a distance from the base region, which distance is substantially less than the distance between the openings in the conical wall portion and the opening at the tip to enable the cleansing liquid to circulate effectively within the vagina;

the openings in the conical wall portion communicating with the side pipe connector, and the tip opening communicating with the central pipe connector;

the device being such that in use incoming and outgoing cleansing liquid do not mix in the device;

the first and second parts being a snap fit together and easily separable for cleaning purposes such that the first and second parts so fit together that the isolated spaces are all times separate to ensure no leakage between them.

2. Vaginal cleansing and hydromassaging device as claimed in claim 1, wherein the side pipe connector and the central pipe connector are of the same size.

3. Vaginal cleansing and hydromassaging device as claimed in claim 1, comprising a high-density polypropylene.

* * * * *